(12) United States Patent
Hamano et al.

(10) Patent No.: US 10,433,541 B2
(45) Date of Patent: Oct. 8, 2019

(54) ANTIBACTERIAL LIQUID, ANTIBACTERIAL FILM, AND WET WIPE

(71) Applicant: FUJIFILM Corporation, Tokyo (JP)

(72) Inventors: Mitsumasa Hamano, Shizuoka (JP); Naohiro Matsunaga, Shizuoka (JP); Yusuke Hatanaka, Shizuoka (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/801,909

(22) Filed: Nov. 2, 2017

(65) Prior Publication Data

US 2018/0116208 A1     May 3, 2018

Related U.S. Application Data

(63) Continuation of application No. PCT/JP2016/064369, filed on May 13, 2016.

(30) Foreign Application Priority Data

May 15, 2015 (JP) ................... 2015-100493
Dec. 14, 2015 (JP) ................... 2015-242880

(51) Int. Cl.
| | | |
|---|---|---|
| *A01N 25/04* | (2006.01) | |
| *A01N 25/34* | (2006.01) | |
| *A01N 31/02* | (2006.01) | |
| *A01N 59/16* | (2006.01) | |
| *A47L 13/17* | (2006.01) | |

(52) U.S. Cl.
CPC ............. *A01N 25/04* (2013.01); *A01N 25/34* (2013.01); *A01N 31/02* (2013.01); *A01N 59/16* (2013.01); *A47L 13/17* (2013.01)

(58) Field of Classification Search
CPC ........ A01N 25/34; A01N 31/02; A01N 25/24; A01N 25/04; A01N 59/16; A01N 25/10; A47L 13/17
See application file for complete search history.

(56) References Cited

U.S. PATENT DOCUMENTS

| | | | | |
|---|---|---|---|---|
| 5,141,803 A | * | 8/1992 | Pregozen | A61K 8/0208 15/104.93 |
| 5,863,679 A | | 1/1999 | Tsushima et al. | |
| 2004/0106533 A1 | * | 6/2004 | Mitra | C11D 1/62 510/183 |
| 2009/0155327 A1 | * | 6/2009 | Martin | A47L 13/16 424/404 |

FOREIGN PATENT DOCUMENTS

| | | | |
|---|---|---|---|
| CN | 104312396 A | 1/2015 | |
| JP | 07047282 A | 2/1995 | |
| JP | H10-168349 A | 6/1998 | |
| JP | H11-279540 A | 10/1999 | |
| JP | 11279540 | * 11/1999 | ............ A01N 25/08 |
| JP | 2001219664 A | 8/2001 | |
| JP | 2002023336 A | 1/2002 | |
| JP | 2003-136054 A | 5/2003 | |
| JP | 2003162924 A | 6/2003 | |
| JP | 2003-206139 A | 7/2003 | |
| JP | 2003-286115 A | 10/2003 | |
| JP | 2004262941 A | 9/2004 | |
| JP | 2005-060695 A | 3/2005 | |
| JP | 2007308442 A | 11/2007 | |
| JP | 2009035620 A | 2/2009 | |
| JP | 2009035621 A | 2/2009 | |
| JP | 2013-129611 A | 7/2013 | |

OTHER PUBLICATIONS

Nakagawa et al. (JPH11279540A English translation provided by Google Patents) 1999 (Year: 1999).*
Notification of Reasons for Refusal, dated Feb. 6, 2018, in related Japanese Application No. 2016-095476, 8 pages in English and Japanese.
International Search Report for PCT/JP2016/064369 dated Aug. 2, 2016 [PCT/ISA/210].
Written Opinion of the International Searching Authority dated Aug. 2, 2016, in counterpart International Application No. PCT/JP2016/064369.
International Preliminary Report on Patentability dated Nov. 21, 2017, in counterpart International Application No. PCT/JP2016/064369.
Communication dated Feb. 21, 2018 from the European Patent Office in counterpart European application No. 16796444.4.
Communication pursuant to Article 94(3) EPC, dated Apr. 18, 2019, issued in corresponding European Patent Application No. 16796444.4, 7 pages.

* cited by examiner

*Primary Examiner* — Ernst V Arnold
(74) *Attorney, Agent, or Firm* — Sughrue Mion, PLLC

(57) ABSTRACT

Provided are an antibacterial liquid having excellent sedimentation resistance, an antibacterial film formed using the antibacterial liquid, and a wet wipe produced using the antibacterial liquid. The antibacterial liquid is an antibacterial liquid including antibacterial microparticles, a binder, and a solvent, in which the antibacterial microparticles contain a silver-supporting inorganic oxide, the average particle size of the antibacterial microparticles is 1.0 μm or less, the binder includes at least one silane compound, the solvent includes an alcohol and water, and the content of the alcohol with respect to the total mass of the antibacterial liquid is 10% by mass or more.

23 Claims, 1 Drawing Sheet

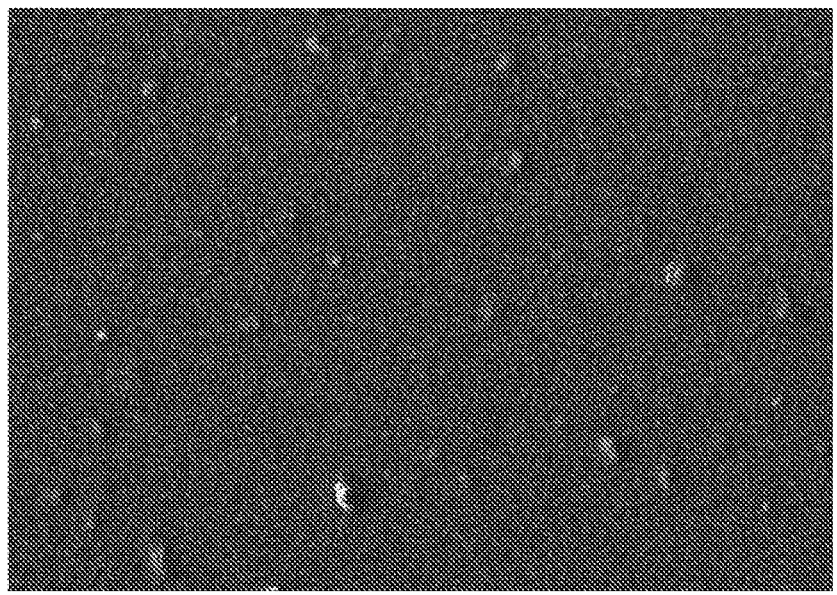

ANTIBACTERIAL LIQUID, ANTIBACTERIAL FILM, AND WET WIPE

CROSS-REFERENCE TO RELATED APPLICATIONS

This application is a Continuation of PCT International Application No. PCT/JP2016/064369 filed on May 13, 2016, which claims priority under 35 U.S.C. § 119(a) to Japanese Patent Application No. 2015-100493 filed on May 15, 2015 and Japanese Patent Application No. 2015-242880 filed on Dec. 14, 2015. Each of the above applications is hereby expressly incorporated by reference, in its entirety, into the present application.

BACKGROUND OF THE INVENTION

1. Field of the Invention

The present invention relates to an antibacterial liquid, an antibacterial film, and a wet wipe.

2. Description of the Related Art

In the related art, as one kind of antibacterial microparticles, for example, JP2003-206139A discloses "antibacterial glass microspheres containing an antibacterial metal in the glass composition, the glass microspheres having an average particle size of a specific value of 0.05 to 5.0 μm, with the standard deviation of the particle size being ±0.08 μm or less with respect to the specific value".

SUMMARY OF THE INVENTION

The inventors of the present invention conducted an investigation on liquids containing antibacterial microparticles (antibacterial liquids). As a result, the inventors found that there are cases in which the antibacterial microparticles in an antibacterial liquid are likely to sediment (that is, cases in which sedimentation resistance is insufficient). In a case in which an antibacterial liquid has insufficient sedimentation resistance, the antibacterial liquid is denatured in a short period of time, and there is a possibility that there may be problems with antibacterial properties and coatability.

Thus, an object of the invention is to provide an antibacterial liquid having excellent sedimentation resistance, an antibacterial film formed using the antibacterial liquid, and a wet wipe produced using the antibacterial liquid.

The inventors of the present invention conducted a thorough investigation, and as a result, the inventors found that the object is achieved by adjusting the average particle size of the antibacterial microparticles to a particular range and using a particular solvent, thus completing the invention.

That is, the invention provides the following items [1] to [21].

[1] An antibacterial liquid comprising: an antibacterial microparticle; a binder; and a solvent, wherein the antibacterial microparticle contains a silver-supporting inorganic oxide, the average particle size of the antibacterial microparticles is 1.0 μm or less, the binder includes at least one silane compound, the solvent includes an alcohol and water, and the content of the alcohol is 10% by mass or more with respect to the total mass of the antibacterial liquid.

[2] The antibacterial liquid according to [1], wherein the average particle size of the antibacterial microparticles is 0.7 μm or less.

[3] The antibacterial liquid according to [1] or [2], wherein the silver-supporting inorganic oxide is silver-supporting glass.

[4] The antibacterial liquid according to any one of [1] to [3], wherein the content of the alcohol is 50% by mass or more with respect to the total mass of the antibacterial liquid.

[5] The antibacterial liquid according to any one of [1] to [4], wherein the content of the antibacterial microparticles is, as solid content, 1.0% by mass or less with respect to the total mass of the antibacterial liquid.

[6] The antibacterial liquid according to any one of [1] to [5], wherein the content of the antibacterial microparticles is, as solid content, 0.2% by mass or less with respect to the total mass of the antibacterial liquid.

[7] The antibacterial liquid according to any one of [1] to [6], wherein the content of the antibacterial microparticles is, as solid content, 20% by mass or less with respect to the total solid content mass of the antibacterial liquid.

[8] The antibacterial liquid according to any one of [1] to [7], wherein the viscosity at 25° C. is 0.5 to 5 cP.

[9] The antibacterial liquid according to any one of [1] to [8], wherein the turbidity is 100 ppm or less.

[10] The antibacterial liquid according to any one of [1] to [9], further comprising an anionic dispersant.

[11] The antibacterial liquid according to [10], wherein the content of the anionic dispersant is 50% by mass or more with respect to the content of the antibacterial microparticles.

[12] The antibacterial liquid according to any one of [1] to [11], wherein in a case in which the antibacterial liquid is stored for 500 hours in a low-temperature environment at a temperature of 5° C., the amount of change in the viscosity at 25° C. is 2 cP or less, and the amount of change in the turbidity is 10 ppm or less.

[13] The antibacterial liquid according to any one of [1] to [12], wherein in a case in which the antibacterial liquid is stored for 500 hours in a high-temperature environment at a temperature of 40° C. and a relative humidity of 80%, the amount of change in the viscosity at 25° C. is 2 cP or less, and the amount of change in the turbidity is 20 ppm or less.

[14] The antibacterial liquid according to any one of [1] to [13], wherein the absolute value of the difference between the water contact angle X of a first antibacterial film formed by applying the antibacterial liquid on a base material and the water contact angle Y of a second antibacterial film formed by applying the antibacterial liquid on the first antibacterial film, |X−Y|, is 10° or less.

[15] The antibacterial liquid according to any one of [1] to [14], wherein the antibacterial liquid has a pH of 6 or lower.

[16] An antibacterial film formed using the antibacterial liquid according to any one of [1] to [15].

[17] The antibacterial film according to [16], wherein the antibacterial film has a water contact angle of 60° or less.

[18] The antibacterial film according to [16] or [17], wherein the antibacterial microparticles are disposed in a convex shape.

[19] The antibacterial film according to any one of [16] to [18], wherein the ratio B/A of the average particle size B of the antibacterial microparticles with respect to the film thickness A is 1 or greater.

[20] The antibacterial film according to any one of [16] to [19], wherein the antibacterial film has a film thickness of 1.0 μm or less.

[21] A wet wipe comprising a base fabric impregnated with the antibacterial liquid according to any one of [1] to [15].

According to the invention, an antibacterial liquid having excellent sedimentation resistance, an antibacterial film formed using the antibacterial liquid, and a wet wipe produced using the antibacterial liquid can be provided.

BRIEF DESCRIPTION OF THE DRAWING

FIG. 1 is an electron micrograph of the surface of Antibacterial Film B-8 of Example 8 captured (magnification ratio: 5,000 times) by a scanning electron microscope.

DESCRIPTION OF THE PREFERRED EMBODIMENTS

Hereinafter, the antibacterial liquid, antibacterial film, and wet wipe of the invention will be described.

A numerical value range expressed using the symbol "~" in the present specification means a range including the numerical values described before and after the symbol "~" as the lower limit and the upper limit.

[Antibacterial Liquid]

The antibacterial liquid of the invention is an antibacterial liquid comprising antibacterial microparticles, a binder, and a solvent, in which the antibacterial microparticles contain a silver-supporting inorganic oxide, the average particle size of the antibacterial microparticles is 1.0 µm or less, the binder includes at least one silane compound, the solvent includes an alcohol and water, and the content of the alcohol with respect to the total mass of the antibacterial liquid is 10% by mass or more.

The antibacterial liquid of the invention is such that the antibacterial microparticles do not easily sediment, and the antibacterial liquid has excellent sedimentation resistance. Therefore, in the antibacterial liquid of the invention, denaturation is suppressed over a long time period. This is speculated to be because, for example, aggregation is suppressed since the average particle size of the antibacterial microparticles is small, and the aggregation proportion of the antibacterial microparticles is decreased by the alcohol included in the solvent.

Hereinafter, the various components included in the antibacterial liquid of the invention will be described in detail.

[Antibacterial Microparticles]

The antibacterial microparticles contain at least a silver-supporting inorganic oxide. The average particle size of the antibacterial microparticles is 1.0 µm or less.

<Silver-Supporting Inorganic Oxide>

The silver-supporting inorganic oxide has silver, and an inorganic oxide serving as a support that supports this silver.

Regarding the silver (silver atoms), there are no particular limitations on the type of silver. The form of silver is also not particularly limited, and for example, silver is incorporated in the form of metal silver, silver ion, or a silver salt (including a silver complex). According to the present specification, a silver complex is included in the scope of silver salts.

Examples of the silver salt include silver acetate, silver acetylacetonate, silver azide, silver acetylide, silver arsenate, silver benzoate, silver hydrogen fluoride, silver bromate, silver bromide, silver carbonate, silver chloride, silver chlorate, silver chromate, silver citrate, silver cyanate, silver cyanide, silver (cis,cis-1,5-cyclooctadiene)-1,1,1,5,5,5-hexafluoroacetylacetonate, silver diethyldithiocarbamate, silver(I) fluoride, silver(II) fluoride, silver 7,7-dimethyl-1,1,1,2,2,3,3,-heptafluoro-4,6-octanedionate, silver hexafluoroantimonate, silver hexafluoroarsenate, silver hexafluorophosphate, silver iodate, silver iodide, silver isothiocyanate, potassium silver cyanide, silver lactate, silver molybdate, silver nitrate, silver nitrite, silver(I) oxide, silver(II) oxide, silver oxalate, silver perchlorate, silver perfluorobutyrate, silver perfluoropropionate, silver permanganate, silver perrhenate, silver phosphate, silver picrate monohydrate, silver propionate, silver selenate, silver selenide, silver selenite, sulfadiazine silver, silver sulfate, silver sulfide, silver sulfite, silver telluride, silver tetrafluoroborate, silver tetraiodomercurate, silver tetratungstate, silver thiocyanate, silver p-toluenesulfonate, silver trifluoromethanesulfonate, silver trifluoroacetate, and silver vanadate.

Examples of the silver complex include a histidine-silver complex, a methionine-silver complex, a cysteine-silver complex, an aspartic acid-silver complex, a pyrrolidone carboxylic acid-silver complex, an oxotetrahydrofurancarboxylic acid-silver complex, and an imidazole-silver complex.

Meanwhile, examples of the inorganic oxide as a support include zinc calcium phosphate, calcium phosphate, zirconium phosphate, aluminum phosphate, calcium silicate, activated carbon, activated alumina, silica gel, glass (at least one compound selected from the group consisting of silicon oxide, phosphorus oxide, magnesium oxide, sodium oxide, aluminum oxide, zinc oxide, calcium oxide, boron oxide, and potassium oxide), zeolite, apatite, hydroxyapatite, titanium phosphate, potassium titanate, hydrous bismuth oxide, hydrous zirconium oxide, and hydrotalcite.

Suitable examples of such a silver-supporting inorganic oxide include silver-supporting zeolite, silver-supporting apatite, silver-supporting glass, silver-supporting zirconium phosphate, and silver-supporting calcium silicate. Among them, silver-supporting apatite and silver-supporting glass are preferred, and from the viewpoint of antibacterial properties, silver-supporting glass is more preferred.

The antibacterial microparticles may also contain an antibacterial agent other than the silver-supporting inorganic oxide, and examples thereof include an organic antibacterial agent, and an inorganic antibacterial agent that does not contain silver.

Examples of the organic antibacterial agent include a phenol ether derivative, an imidazole derivative, a sulfone derivative, an N-haloalkylthio compound, an anilide derivative, a pyrrole derivative, a quaternary ammonium salt, a pyridine-based compound, a triazine-based compound, a benzisothiazoline-based compound, and an isothiazoline-based compound.

Examples of the inorganic antibacterial agent that does not contain silver include antibacterial agents having a metal such as copper or zinc supported on the above-mentioned supports.

The antibacterial microparticles may be in the form of microparticles containing an antibacterial agent other than the silver-supporting inorganic oxide, or may also be in the form of microparticles substantially formed from a silver-supporting inorganic oxide only.

The content of the silver-supporting inorganic oxide in the antibacterial microparticles is, as solid content, preferably 60% by mass or more, more preferably 70% by mass or more, and even more preferably 95% by mass or more.

<Average Particle Size of Antibacterial Microparticles>

The average particle size of the antibacterial microparticles is 1.0 µm or less, and for the reason that the antibacterial microparticles can have superior sedimentation resistance, the average particle size is preferably 0.9 µm or less, and more preferably 0.7 μm or less. The lower limit is not particularly limited; however, for example, the lower limit is 0.05 μm or more.

According to the invention, the average particle size is obtained by measuring the 50% volume cumulative diameter (D50) three times using a laser diffraction/scattering type particle size distribution analyzer manufactured by Horiba, Ltd., and the average value of the values obtained by measuring three times is used.

The average particle size of the antibacterial microparticles can be regulated by a conventionally known method, and for example, dry pulverization or wet pulverization can be employed. In regard to dry pulverization, for example, a mortar, a jet mill, a hammer mill, a pin mill, a rotary mill, a vibratory mill, a planetary mill, a beads mill, or the like is used as appropriate. Furthermore, in regard to wet pulverization, various ball mills, a high-speed rotating pulverizer, a jet mill, a beads mill, an ultrasound homogenizer, a high-pressure homogenizer, or the like is used as appropriate.

For example, in regard to a beads mill, the average particle size can be controlled by regulating the diameter, kind, mixing amount, and the like of the beads that serve as media.

According to the invention, for example, the average particle size of the antibacterial microparticles can be regulated by wet pulverization by dispersing the antibacterial microparticles as an object of pulverization in ethanol or water, and mixing and vibrating zirconia beads having different sizes. However, the method is not limited to this method, and any appropriate method for controlling the particle size may be selected.

<Content of Antibacterial Microparticles>

The content of the antibacterial microparticles with respect to the total mass of the antibacterial liquid of the invention is, as solid content, for example, 1.5% by mass or less, and from the viewpoint of sedimentation resistance, the content is preferably 1.0% by mass or less, more preferably 0.2% by mass or less, and even more preferably 0.1% by mass or less. The lower limit is not particularly limited; however, for example, the lower limit is 0.0001% by mass or more.

Furthermore, in a case in which application of an antibacterial liquid and formation of a coating film (antibacterial film) are repeatedly carried out (hereinafter, this action will be referred to as "overcoating") using a wet wipe that is obtained by impregnating a base fabric with the antibacterial liquid of the invention, or the like, for the reason that whitening of the antibacterial film obtainable by this overcoating can be suppressed, the content of the antibacterial microparticles with respect to the total mass of the antibacterial liquid of the invention is, as solid content, preferably 0.2% by mass or less, and more preferably 0.01% by mass or less.

In an actual environment, it is assumed that the antibacterial film is peeled off little by little as the surface of the antibacterial film is touched or rubbed by a human being or an object, and therefore, it may be considered that the influence of whitening is small. However, in an environment in which application of the antibacterial liquid is performed continuously (for example, every day), such as in a case in which a cleaning operation is carried out using a wet wipe or the like, suppression of whitening may be required.

The content of the antibacterial microparticles with respect to the total solid content mass of the antibacterial liquid of the invention is, as solid content, for example, 25% by mass or less, and from the viewpoint of sedimentation resistance, the content is preferably 20% by mass or less, more preferably 4% by mass or less, and even more preferably 3% by mass or less. The lower limit is not particularly limited; however, for example, the lower limit is 0.1% by mass or more.

The content of silver in the antibacterial microparticles is not particularly limited; however, the content is, for example, 0.1% to 30% by mass, and preferably 0.3% to 10% by mass, with respect to the total mass of the antibacterial microparticles.

[Binder]

The binder includes at least one silane compound. In addition, it is preferable that the binder exhibits hydrophilicity.

<Silane Compound>

Regarding the silane compound, for example, a siloxane compound (siloxane oligomer) represented by General Formula (1') may be mentioned.

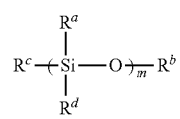

(1')

Here, in General Formula (1'), $R^a$, $R^b$, $R^c$, and $R^d$ each independently represent a hydrogen atom or an organic group. m represents an integer from 1 to 100. $R^a$ to $R^d$ may be respectively identical with or different from each other, and $R^a$ to $R^d$ may also be bonded to each other and form a ring.

Examples of the organic group represented by $R^a$ to $R^d$ include an alkyl group having 1 to 20 carbon atoms, an aryl group having 6 to 20 carbon atoms, and a heterocyclic group having 4 to 16 carbon atoms.

For $R^a$ to $R^d$, a hydrogen atom, an alkyl group having 1 to 12 carbon atoms, or an aryl group having 6 to 14 carbon atoms is preferred, and a hydrogen atom, an alkyl group having 1 to 6 carbon atoms, or an aryl group having 6 to 10 carbon atoms is more preferred. The alkyl group represented by $R^a$ to $R^d$ may be branched. The organic group represented by $R^a$ to $R^d$ may have a substituent, and this substituent may further have a substituent.

Specific preferred examples of $R^a$ to $R^d$ include a hydrogen atom, a methyl group, an ethyl group, a propyl group, a butyl group, an isopropyl group, an n-butyl group, a tert-butyl group, an n-pentyl group, an n-hexyl group, a cyclohexyl group, a phenyl group, and a naphthyl group.

m is preferably 2 to 20, more preferably 3 to 15, and even more preferably 5 to 10.

Regarding the silane compound, from the viewpoint of obtaining an antibacterial film exhibiting hydrophilicity and having excellent antibacterial properties, for example, a silane compound having an alkoxy group having 1 to 6 carbon atoms, such as a methoxy group or an ethoxy group, may be mentioned, and a siloxane compound (siloxane oligomer) represented by General Formula (1) is preferred.

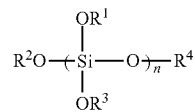

(1)

Here, in General Formula (1), $R^1$ to $R^4$ each independently represent an organic group having 1 to 6 carbon atoms. n represents an integer from 1 to 100. The organic group may be linear or branched.

In General Formula (1), $R^1$ to $R^4$ each independently represent an organic group having 1 to 6 carbon atoms. $R^1$ to $R^4$ may be respectively identical with or different from each other. $R^1$ to $R^4$ may be linear, or may be branched. The organic group represented by $R^1$ to $R^4$ is preferably an alkyl group having 1 to 6 carbon atoms. Examples of the alkyl group represented by $R^1$ to $R^4$ include a methyl group, an ethyl group, a propyl group, an isopropyl group, an n-butyl group, a tert-butyl group, an n-pentyl group, an n-hexyl group, and a cyclohexyl group. By adjusting the number of carbon atoms of the alkyl group represented by $R^1$ to $R^4$ to 1 to 6, the hydrolyzability of the siloxane oligomer can be increased. In view of the ease of hydrolysis, the organic group represented by $R^1$ to $R^4$ is more preferably an alkyl group having 1 to 4 carbon atoms, and even more preferably an alkyl group having 1 or 2 carbon atoms.

In General Formula (1), n is preferably an integer from 2 to 20. By adjusting n to be within this range, the viscosity of a solution including the hydrolysate can be adjusted to an appropriate range, and the reactivity of the siloxane oligomer can be controlled to be in a preferred range. In a case in which n is greater than 20, the viscosity of a solution including the hydrolysate of the siloxane oligomer increases too high, and handling may be difficult. On the other hand, in a case in which n is 1, control of the reactivity of the alkoxysilane is difficult, and it may be difficult to exhibit hydrophilicity after coating. n is more preferably 3 to 15, and even more preferably 5 to 10.

The siloxane oligomer is brought to a state in which at least a portion thereof is hydrolyzed, as the siloxane oligomer is mixed together with an aqueous component. A hydrolysate of a siloxane oligomer is obtained by reacting the siloxane oligomer with an aqueous component, and changing the alkoxy group bonded to a silicon atom to a hydroxyl group. On the occasion of hydrolysis, it is not necessarily essential that all alkoxy groups react; however, in order to exhibit hydrophilicity after coating, it is preferable that as many alkoxy groups as possible are hydrolyzed. The amount of the aqueous component needed at the minimum on the occasion of hydrolysis is an amount equimolar to that of the alkoxy groups of the siloxane oligomer; however, in order to carry out the reaction smoothly, it is preferable that a large excess of water is present.

This hydrolysis reaction proceeds at room temperature; however, the reaction system may be heated for accelerating the reaction. It is preferable that the reaction time is longer, because the reaction may proceed further. Furthermore, it is also possible to obtain a hydrolysate for a time period of about half a day in a case in which the catalyst that will be described below is present.

The hydrolysis reaction is a reversible reaction, and as water is excluded from the system, the hydrolysate of the siloxane oligomer initiates condensation between hydroxyl groups. Therefore, in a case in which an aqueous solution of the hydrolysate is obtained by reacting the siloxane oligomer with a large excess of water, it is preferable to use the hydrolysate in the form of an aqueous solution, without forcibly isolating the hydrolysate from the aqueous solution.

The antibacterial liquid of the invention includes water as a solvent; however, as an aqueous component is used as a solvent, the burden on the health of the operator at the time of handling and the burden on the environment are reduced, and also, the hydrolysate of the siloxane oligomer being condensed in the liquid during storage can be suppressed.

Regarding the siloxane oligomer represented by General Formula (1), a commercially available product can be used, and specific examples include MKC (registered trademark) SILICATE manufactured by Mitsubishi Chemical Corporation.

The binder may include a binder other than the above-mentioned silane compound, or may substantially include the above-mentioned silane compound only.

The content of the silane compound in the binder is preferably 70% by mass or more, more preferably 80% by mass or more, and even more preferably 90% by mass or more.

<Content of Binder>

The content of the binder with respect to the total solid content mass of the antibacterial liquid of the invention is preferably 3% to 95% by mass, more preferably 5% to 90% by mass, and even more preferably 10% to 85% by mass.

The content of the binder with respect to the total mass of the antibacterial liquid of the invention is preferably 10% by mass or less, more preferably 5% by mass or less, and even more preferably 3% by mass or less.

[Solvent]

The solvent includes an alcohol and water. Water is not particularly limited, and for example, pure water may be used.

The alcohol is preferable because the alcohol annihilates a wide variety of microorganisms in a short time period.

There are no particular limitations on the alcohol; however, for example, a chain-like lower hydrocarbon alcohol (hereinafter, "lower alcohol") may be used. Suitable examples of the lower alcohol include a lower alcohol having 1 to 6 carbon atoms, and specific examples thereof include methanol, ethanol, n-propanol, isopropanol, n-butanol, 2-butanol, i-butanol, t-butanol, n-pentanol, t-amyl alcohol, and n-hexanol. These may be used singly, or two or more kinds thereof may be used in combination.

Among these, methanol, ethanol, isopropanol, butanol, or n-propanol is preferred, and ethanol or isopropanol is more preferred.

The alcohol may also be a higher alcohol. Suitable examples of the higher alcohol include higher alcohols having 7 or more carbon atoms (preferably, 7 to 15 carbon atoms), and specific examples thereof include capryl alcohol, lauryl alcohol, and myristyl alcohol.

Examples of the alcohol other than those described above include phenyl ethyl alcohol, ethylene glycol, ethylene glycol mono-n-butyl ether, diethylene glycol mono-n-butyl ether, triethylene glycol mono-n-butyl ether, tetraethylene glycol mono-n-butyl ether, and dipropylene glycol monobutyl ether.

These may be used singly, or two or more kinds thereof may be used in combination.

From the viewpoint of sedimentation resistance, the content of the alcohol with respect to the total mass of the antibacterial liquid of the invention is 10% by mass or more, preferably 50% by mass or more, more preferably 65% by mass or more, and even more preferably 80% by mass or more. The upper limit is not particularly limited; however, the upper limit is 99% by mass or less.

The content of the alcohol in the solvent is, for example, 5% to 100% by mass, preferably 30% to 95% by mass, and more preferably 40% to 95% by mass.

The content of the total solid content mass with respect to the total mass of the antibacterial liquid of the invention is preferably 0.0005% to 30% by mass, more preferably 0.01% to 20% by mass, and even more preferably 0.05% to 10% by mass.

For the reason that whitening of an antibacterial film obtainable by overcoating can be suppressed, the content of the total solid content mass with respect to the total mass of the antibacterial liquid of the invention is preferably 10% by mass or less, and more preferably 1% by mass or less.

The solvent may also include another hydrophilic organic solvent apart from an alcohol. Examples of the other hydrophilic organic solvent include benzole, toluole, methyl ethyl ketone (MEK), acetone, a 10% denatonium benzoate alcohol solution, ethyl acetate, hexane, ethyl ether, geraniol, 8-acetylated sucrose, brucine, linalool, linalyl acetate, acetic acid, and butyl acetate.

In a case in which another hydrophilic organic solvent is included in the solvent in addition to an alcohol, the content of the other hydrophilic organic solvent in the solvent apart from an alcohol is, for example, preferably 20% by mass or less.

Above all, it is preferable that the solvent substantially includes an alcohol and water.

According to the invention, diluents (water, an alcohol, and the like) of various components are also included in the solvent.

[Dispersant]

It is preferable that the antibacterial liquid of the invention includes a dispersant, from the viewpoint of increasing the dispersibility of the antibacterial microparticles and improving sedimentation resistance. As the dispersant, a nonionic or anionic dispersant is preferably used. From the viewpoint of the affinity to the antibacterial microparticles, for example, a dispersant having an anionic polar group such as a carboxyl group, a phosphoric acid group, or a hydroxyl group (anionic dispersant) is more preferred.

Regarding the anionic dispersant, a commercially available product can be used, and specific suitable examples thereof include trade name DISPERBYK (registered trademark)-110, -111, -116, -140, -161, -162, -163, -164, -170, -171, -174, -180, and -182 of BYK-Chemie GmbH.

The content of the dispersant (particularly, anionic dispersant) is, as solid content, for example, 50% by mass or more with respect to the content of the antibacterial microparticles, and for the reason that sedimentation resistance is further improved, the content is preferably 200% by mass or more, and more preferably 400% by mass or more. Meanwhile, the upper limit is not particularly limited; however, for example, the upper limit is 1,500% by mass or less.

[Catalyst]

In a case in which the antibacterial liquid of the invention includes the above-mentioned siloxane oligomer as a binder, it is preferable that the antibacterial liquid further includes a catalyst that accelerates condensation thereof. By applying the antibacterial liquid of the invention, and then eliminating moisture therefrom by drying the applied liquid, (at least a portion of) the hydroxyl groups carried by the hydrolysate of the siloxane oligomer are condensed with each other to form bonds, and a stable coating film (antibacterial film) is obtained. At this time, the formation of the antibacterial film can be made to proceed more rapidly by incorporating a catalyst that accelerates condensation of the siloxane oligomer.

There are no particular limitations on the catalyst that accelerates condensation of the siloxane oligomer; however, examples include an acid catalyst, an alkali catalyst, and an organometallic catalyst. Examples of the acid catalyst include nitric acid, hydrochloric acid, sulfuric acid, acetic acid, chloroacetic acid, formic acid, oxalic acid, and toluenesulfonic acid. Examples of the alkali catalyst include sodium hydroxide, potassium hydroxide, and tetramethylammonium hydroxide. Examples of the organometallic catalyst include aluminum chelate compounds such as aluminum bis(ethyl acetoacetate) mono(acetylacetonate), aluminum tris(acetylacetonate), and aluminum ethyl acetoacetate diisopropylate; zirconium chelate compounds such as zirconium tetrakis(acetylacetonate) and zirconium bis(butoxy) bis(acetylacetonate); titanium chelate compounds such as titanium tetrakis(acetylacetonate) and titanium bis(butoxy) bis(acetylacetonate); and organotin compounds such as dibutyltin diacetate, dibutyltin dilaurate, and dibutyltin dioctoate.

Among these, an organometallic catalyst is preferred, and an aluminum chelate compound or a zirconium chelate compound is more preferred.

The content of the catalyst that accelerates the condensation of the siloxane oligomer is, as solid content, preferably 0.1% to 20% by mass, more preferably 0.2% to 15% by mass, and even more preferably 0.3% to 10% by mass, with respect to the total solid content mass of the antibacterial liquid of the invention.

The catalyst that accelerates the condensation of the siloxane oligomer is also useful for the hydrolysis of the siloxane oligomer.

[Surfactant]

The antibacterial liquid of the invention may also include a surfactant (component that exhibits interface activity). Thereby, coatability can be increased, and the surface tension is decreased so that more uniform coating is enabled.

Regarding the surfactant, a nonionic surfactant and an ionic (anionic, cationic, or amphoteric) surfactant can all be suitably used. In a case in which an ionic surfactant is added in excess, the amount of electrolyte in the system increases, and aggregation of silica microparticles and the like may be brought about. Therefore, in the case of using an ionic surfactant, it is preferable that the antibacterial liquid further includes a nonionic component that exhibits interface activity.

Examples of the nonionic surfactant include polyalkylene glycol monoalkyl ethers, polyalkylene glycol monoalkyl esters, and polyalkylene glycol monoalkyl ester/monoalkyl ethers. More specific examples include polyethylene glycol monolauryl ether, polyethylene glycol monostearyl ether, polyethylene glycol monocetyl ether, polyethylene glycol monolauryl ester, and polyethylene glycol monostearyl ester.

Examples of the ionic surfactant include anionic surfactants such as an alkyl sulfate, an alkyl benzenesulfonate, and an alkyl phosphate; cationic surfactants such as an alkyl trimethylammonium salt and a dialkyl dimethylammonium salt; and amphoteric surfactants such as an alkylcarboxybetaine.

The content of the surfactant with respect to the total mass of the antibacterial liquid of the invention is, as solid content, for example, 0.0001% by mass or more, preferably 0.001% by mass or more, and more preferably 0.003% by mass or more.

Meanwhile, the content of the surfactant with respect to the total solid content mass of the antibacterial liquid of the invention is, as solid content, preferably 10% by mass or less, more preferably 8% by mass or less, and even more preferably 5% by mass or less.

[Silica Particles]

The antibacterial liquid of the invention may include silica particles. The silica particles allow the antibacterial liquid to exhibit hydrophilicity more effectively, while increasing the physical tolerance of the antibacterial film formed using the antibacterial liquid of the invention. That is, silica particles accomplish the role as a hard filler, and also contribute to hydrophilicity by means of the hydroxyl groups on the surface of the silica particles.

The shape of the silica particles is not particularly limited, and examples include a spherical shape, a plate shape, a needle shape, and a necklace shape; however, a spherical shape is preferred. Furthermore, it is acceptable that the silica particles have silica in the shell, and have air, an organic resin, and the like in the core. The surface of the silica particles may also be subjected to a surface treatment for the purpose of dispersion stabilization.

The average particle size (primary particle size) of the silica particles is preferably 100 nm or less, more preferably 50 nm or less, and even more preferably 30 nm or less. The particle size of the silica particles can be measured in the same manner as in the case of the antibacterial microparticles described above.

It is also acceptable to use two or more kinds of silica particles having different shapes and different sizes in combination.

The content of the silica microparticles with respect to the total solid content mass of the antibacterial liquid of the invention is, as solid content, preferably 0% to 95% by mass, more preferably 10% to 90% by mass, and even more preferably 20% to 80% by mass. The content of the silica microparticles with respect to the total mass of the antibacterial liquid of the invention is, as solid content, preferably 30% by mass or less, more preferably 20% by mass or less, and even more preferably 10% by mass or less.

[Acidic Material]

The antibacterial liquid of the invention may further include an acidic material. The antibacterial liquid of the invention can be imparted with antiviral properties by incorporating an acidic material into the antibacterial liquid.

Examples of the acidic material used in the invention include inorganic acids such as phosphoric acid and sulfuric acid; organic acids such as malic acid, lactic acid, tartaric acid, salicylic acid, gluconic acid, adipic acid, phytic acid, fumaric acid, succinic acid, ascorbic acid, sorbic acid, glyoxylic acid, Meldrum's acid, glutamic acid, picric acid, aspartic acid, acetic acid, formic acid, and citric acid; and alkali metal salts of these acids. These may be used singly, or two or more kinds thereof may be used in combination.

The content of the acidic material in the antibacterial liquid of the invention is not particularly limited, and for example, an appropriate amount of an acidic material is added such that the pH of the antibacterial liquid of the invention will be within the range of pH that will be described below.

[Method for Producing Antibacterial Liquid]

The antibacterial liquid of the invention can further include other additives (for example, a preservative, a deodorizing agent, and a fragrance) as necessary, to the extent that the purpose of the invention is not impaired.

The antibacterial liquid of the invention is obtained by appropriately mixing the above-mentioned essential components and optional components.

[Viscosity of Antibacterial Liquid]

The viscosity of the antibacterial liquid of the invention is not particularly limited. Above all, in a case in which the viscosity is high, sedimentation of the antibacterial microparticles can be further suppressed, while coatability may be deteriorated. Therefore, it is preferable to adjust the viscosity to an appropriate range.

From such a viewpoint, the viscosity at 25° C. of the antibacterial liquid of the invention is preferably 100 cP (centipoises) or less, more preferably 50 cP or less, and even more preferably 0.5 to 5 cP.

According to the invention, the viscosity is measured using VISCOMETER TUB-10 manufactured by Toki Sangyo Co., Ltd., or SEKONIC VISCOMETER manufactured by Sekonic Corporation, and the unit is converted to cP (centipoises).

[Turbidity of Antibacterial Liquid]

The turbidity of the antibacterial liquid of the invention is not particularly limited, and for example, in a case in which the content of the antibacterial microparticles is increased, turbidity increases. However, from the viewpoint of securing transparency at the time of applying the antibacterial liquid of the invention, it is preferable to adjust the turbidity to an appropriate range.

From such a viewpoint, the turbidity of the antibacterial liquid of the invention is preferably 200 ppm or less, more preferably 100 ppm or less, and even more preferably 80 ppm or less. Meanwhile, the lower limit is not particularly limited; however, for example, the lower limit is 1 ppm or more.

According to the invention, the turbidity is measured based on JIS K0101, using an integrating sphere type turbidimeter, PT200, manufactured by Mitsubishi Chemical Analytech Co., Ltd.

[Amounts of Change in Viscosity and Turbidity]

It is preferable that the antibacterial liquid of the invention is not denatured for a long time period.

Specifically, in a case in which the antibacterial liquid of the invention is stored for 500 hours in a low-temperature environment at a temperature of 5° C., it is preferable that the amount of change in the viscosity at 25° C. is 2 cP or less, and the amount of change in the turbidity is 10 ppm or less.

In a case in which the antibacterial liquid of the invention is stored for 500 hours in a high-temperature environment at a temperature of 40° C. and a relative humidity of 80%, it is preferable that the amount of change in the viscosity at 25° C. is 2 cP or less, and the amount of change in the turbidity is 20 ppm or less.

[pH of Antibacterial Liquid]

The pH of the antibacterial liquid of the invention is not particularly limited; however, in a case in which rough handling of the user in an actual use environment or the like is considered, it is preferable to adjust the pH to an appropriate range.

The pH of the antibacterial liquid of the invention is preferably 3 to 10, and more preferably 4 to 9.

In recent years, more emphasis is placed on the management of hygiene management concerning viruses such as norovirus, and from the viewpoint of antiviral properties, it is preferable to adjust the pH of the antibacterial liquid of the invention to 6 or lower.

According to the invention, the pH is measured using a pH meter, HM-30R, manufactured by DKK-Toa Corporation.

[Surface Tension of Antibacterial Liquid]

The surface tension of the antibacterial liquid of the invention is not particularly limited; however, in consideration of wettability at the time of applying the antibacterial liquid of the invention, it is preferable to adjust the surface tension to an appropriate range.

The surface tension of the antibacterial liquid of the invention is preferably 80 mN/m or less, more preferably 60 mN/m or less, and even more preferably 40 mN/m or less.

The lower limit is not particularly limited; however, for example, the lower limit is 5 mN/m or more.

According to the invention, the surface tension is measured using a surface tension meter, DY-300, manufactured by Kyowa Interface Science Co., Ltd.

[Antibacterial Film]

The antibacterial film of the invention is a coating film formed using the antibacterial liquid of the invention, and for example, the antibacterial film can be formed by applying the antibacterial liquid of the invention on a base material, and drying the antibacterial liquid.

The base material on which the antibacterial liquid of the invention is applied is not particularly limited, and glass, a resin, a metal, a ceramic, a fabric, or the like is used as appropriate. Examples of the resin include polypropylene, polystyrene, a polyurethane, an acrylic resin, a polycarbonate, a polyamide, a fluororesin, a latex, polyvinyl chloride, a polyolefin, a melamine resin, an ABS (acrylonitrile-butadiene-styrene) resin, and a polyester (for example, polyethylene terephthalate (PET)). The shape of the base material is not particularly limited, and examples include a plate form, a film form, and a sheet form. The base material surface may be a flat surface, a concave surface, or a convex surface. Furthermore, a conventionally known easily adhesive layer may also be formed on the surface of the base material.

The method for applying the antibacterial liquid of the invention is not particularly limited, and examples include a spraying method, a brush coating method, an immersion method, an electrostatic coating method, a bar coating method, a roll coating method, a flow coating method, a die coating method, a nonwoven fabric coating method, an inkjet method, a casting method, a rotary coating method, and a Langmuir-Blodgett (LB) method.

Regarding the drying after application, drying may be performed at room temperature, or heating to 40° C. to 120° C. may be performed. The drying time is, for example, about 1 to 30 minutes.

[Water Contact Angle of Antibacterial Film]

The water contact angle of the surface of the antibacterial film of the invention is preferably 60° or lower, more preferably 40° or lower, and even more preferably 20° or lower. Thereby, the antibacterial film of the invention has excellent removability of contaminants by washing or the like (antifouling properties), and also exhibits hydrophilicity and excellent antibacterial properties.

Since the antibacterial film exhibits hydrophilicity, moisture can easily permeate into the antibacterial film, and moisture also reaches the antibacterial microparticles (silver-supporting inorganic oxide) in the antibacterial film, so that silver ions can be released. Thus, it is speculated that the antibacterial microparticles in the antibacterial layer can also be effectively utilized thereby, and the supply of silver can be continued, so that satisfactory antibacterial properties are obtained.

The lower limit of the water contact angle is not particularly limited; however, for example, the lower limit is 5° or higher in many cases.

According to the invention, the water contact angle is measured based on the sessile drop method of JIS R3257: 1999. For the measurement, FAMMS DM-701 manufactured by Kyowa Interface Science Co., Ltd. is used. More specifically, 2 μL of liquid droplets are added dropwise using pure water on an antibacterial layer surface that is maintained horizontally, at room temperature of 20° C., and at the time point of 20 seconds after the dropwise addition, the contact angle is measured at 10 sites. The average value of the measurement results is designated as the contact angle.

In a case in which the antibacterial properties of the antibacterial film (first antibacterial film) formed on a base material using the antibacterial liquid of the invention have been deteriorated, double coating may be performed. That is, a second antibacterial film may be formed using the same antibacterial liquid of the invention on the first antibacterial film. At this time, it is preferable that the physical properties of the second antibacterial film are not affected by the first antibacterial film.

For example, it is preferable that the absolute value of the difference between the water contact angle X of a first antibacterial film formed by applying the antibacterial liquid of the invention on a base material and the water contact angle Y of a second antibacterial film formed by applying the antibacterial liquid on this first antibacterial film, $|X-Y|$, is 10° or less, from the viewpoint of stably maintaining antifouling properties.

[Film Thickness of Antibacterial Film]

Since the average particle size of the antibacterial microparticles included in the antibacterial liquid of the invention is small, such as an average particle size of 1.0 μm or less, in a case in which the film thickness of the antibacterial film of the invention formed using this is too large, the antibacterial microparticles are embedded therein, and the antibacterial properties are not easily manifested. Therefore, the film thickness (average film thickness) of the antibacterial film of the invention is preferably 1.0 μm or less, and more preferably 0.5 μm or less. The lower limit of the film thickness is not particularly limited; however, for example, the lower limit is 0.01 μm or more.

According to the invention, the film thickness is determined as follows. First, a sample specimen of an antibacterial film is embedded in a resin, cross-sections are sliced off with a microtome, and the cross-sections thus sliced are observed with a scanning electron microscope. The film thicknesses at any arbitrary ten positions of the antibacterial film are measured, and the value obtained by arithmetically averaging the film thicknesses is designated as the film thickness (average film thickness) of the antibacterial film.

As described above, in a case in which the antibacterial microparticles are embedded in the antibacterial film, the antibacterial properties are not easily manifested. Therefore, it is preferable that the antibacterial microparticles are disposed in a convex shape (the antibacterial microparticles protrude from the surface of the antibacterial film). Specifically, the ratio (B/A) of the average particle size B of the antibacterial microparticles with respect to the film thickness A is preferably 1 or greater, and more preferably 2 or greater.

[Use Applications]

The antibacterial film itself can be used as an antibacterial sheet. Regarding the method of disposing an antibacterial film (antibacterial sheet) in various apparatuses, for example, an antibacterial film may be formed by directly applying the antibacterial liquid of the invention on the surface (front face) of an apparatus, or an antibacterial film may be separately formed and adhered to the surface of an apparatus, with a pressure sensitive adhesive layer or the like being disposed therebetween.

An antibacterial film-attached base material can also be used as a front face plate of various apparatuses.

Examples of apparatuses in which an antibacterial film (antibacterial sheet) and an antibacterial film-attached base material include a radiographic imaging apparatus and a touch panel.

In addition to that, examples of places where the antibacterial liquid of the invention is directly applied in order to suppress cross-infection in medical settings, include walls, ceilings, floors, door knobs, banisters, switches, buttons, and toilet seats in facilities such as hospitals and nursing facilities. Furthermore, since the antibacterial film formed by applying the antibacterial liquid of the invention has superior hydrophilicity, in a case in which contaminants (for example, contaminants such as blood and body fluids) in medical settings adhere to the antibacterial film, the contaminants can be removed simply by mopping up.

[Wet Wipe]

The wet wipe of the invention is a wet wipe having a base fabric impregnated with the antibacterial liquid of the invention. Suitable examples of the base fabric include a nonwoven fabric. The basis weight (mass per unit area) of the base fabric is preferably 100 g/m$^2$ or less. The amount of impregnation at the time of impregnating the base fabric with the antibacterial liquid of the invention is preferably an amount equivalent to one time or more the mass of the base fabric.

The wet wipe of the invention can be used per se as a wet wipe having antibacterial properties. Furthermore, the antibacterial liquid of the invention can be applied on the surface of a base material using the wet wipe of the invention.

EXAMPLES

Hereinafter, the invention will be specifically described by way of Examples. However, the invention is not intended to be limited to these.

Example 1

While 260 g of ethanol was stirred in a vessel, 200 g of pure water, 4.7 g of a siloxane compound as a binder ("MKC (registered trademark) SILICATE MS51" manufactured by Mitsubishi Chemical Corporation), 15 g of ALUMINUM CHELATE D (aluminum bis(ethyl acetoacetate) mono (acetylacetonate), ethanol dilution; solid content concentration: 1% by mass), 60 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 2.2 g of antibacterial microparticles (silver-supporting glass, manufactured by Fuji Chemical Industries Co., Ltd., ethanol dilution; solid content concentration: 50% by mass) having the average particle size controlled to be 1.0 µm were added to the vessel, and the mixture was stirred for 20 minutes. Thus, Antibacterial Liquid A-1 was obtained.

The average particle size of the antibacterial microparticles was regulated in advance by wet pulverization, by mixing the antibacterial microparticles with zirconia beads and vibrating the mixture using a beads mill (hereinafter, the same).

Furthermore, Antibacterial Liquid A-1 was applied, using a bar coater, on a polyethylene terephthalate (PET) base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-1 was obtained as a coating film.

Example 2

The composition of the Antibacterial Liquid A-1 was changed. Specifically, Antibacterial Liquid A-2 was obtained in the same manner as in Example 1, except that the amounts of incorporation were changed to 345 g of ethanol and 115 g of pure water.

Also, Antibacterial Film B-2 was obtained in the same manner as in Example 1, using Antibacterial Liquid A-2.

Example 3

The composition of the Antibacterial Liquid A-1 was changed. Specifically, Antibacterial Liquid A-3 was obtained in the same manner as in Example 1, except that the amounts of incorporation were changed to 427 g of ethanol and 33 g of pure water.

Also, Antibacterial Film B-3 was obtained in the same manner as in Example 1, using Antibacterial Liquid A-3.

Example 4

While 280 g of ethanol was stirred in a vessel, 185 g of pure water, 24 g of a siloxane compound as a binder ("MKC (registered trademark) SILICATE MS51" manufactured by Mitsubishi Chemical Corporation), 60 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 11.5 g of antibacterial microparticles (silver-supporting glass, manufactured by Fuji Chemical Industries Co., Ltd., ethanol dilution; solid content concentration: 50% by mass) having the average particle size controlled to be 1.0 µm were added to the vessel, and the mixture was stirred for 20 minutes. Thus, Antibacterial Liquid A-4 was obtained.

Furthermore, Antibacterial Liquid A-4 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-4 was obtained.

Example 5

While 360 g of ethanol was stirred in a vessel, 94 g of pure water, 15 g of a siloxane compound as a binder ("MKC (registered trademark) SILICATE MS51" manufactured by Mitsubishi Chemical Corporation), 15 g of ALUMINUM CHELATE D (aluminum bis(ethyl acetoacetate) mono (acetylacetonate), ethanol dilution; solid content concentration: 1% by mass), 60 g of a nonionic surfactant ("EMALEX 715" manufactured by Nihon Emulsion Co., Ltd., pure water dilution; solid content concentration: 0.5% by mass), 10 g of an anionic surfactant (sodium di(2-ethylhexyl)sulfosuccinate, pure water dilution; solid content concentration: 0.2% by mass), and 22 g of silica particles ("SNOWTEX O-33" manufactured by Nissan Chemical Industries, Ltd., pure water dilution; solid content concentration: 33% by mass) were sequentially added to the vessel. Subsequently, 2.4 g of antibacterial microparticles (silver-supporting glass, manufactured by Fuji Chemical Industries Co., Ltd., ethanol dilution; solid content concentration: 50% by mass) having the average particle size controlled to be 1.0 µm were added to the vessel, and the mixture was stirred for 20 minutes. Thus, Antibacterial Liquid A-5 was obtained.

Furthermore, Antibacterial Liquid A-5 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-5 was obtained.

Example 6

The Antibacterial Liquid A-5 described above was used.
Antibacterial Liquid A-5 was applied, using a bar coater different from the bar coater used in Example 5, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-6 was obtained.

Example 7

The composition of the Antibacterial Liquid A-5 was changed. Specifically, Antibacterial Liquid A-7 was obtained in the same manner as in Example 5, except that the amounts of incorporation were changed to 384 g of ethanol, 94 g of pure water, 17 g of the siloxane compound binder ("MKC (registered trademark) SILICATE MS51" manufactured by Mitsubishi Chemical Corporation), and 32 g of the silica particles ("SNOWTEX O-33" manufactured by Nissan Chemical Industries, Ltd., pure water dilution; solid content concentration: 33% by mass), and 0.6 g of a dispersant ("DISPERBYK (registered trademark)-180" manufactured by BYK-Chemie GmbH) was added to the mixture.

Furthermore, Antibacterial Liquid A-7 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-7 was obtained.

Example 8

The composition of the Antibacterial Liquid A-7 was changed. Specifically, Antibacterial Liquid A-8 was obtained in the same manner as in Example 7, except that the amounts of incorporation were changed to 360 g of ethanol, 88 g of pure water, 14 g of the siloxane compound binder ("MKC (registered trademark) SILICATE MS51" manufactured by Mitsubishi Chemical Corporation), and 3.6 g of the dispersant ("DISPERBYK (registered trademark)-180" manufactured by BYK-Chemie GmbH), and 15 g of isopropanol was added to the mixture.

Furthermore, Antibacterial Liquid A-8 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-8 was obtained.

Example 9

The composition of the Antibacterial Liquid A-7 was changed. Specifically, Antibacterial Liquid A-9 was obtained in the same manner as in Example 7, except that the amounts of incorporation were changed to 540 g of ethanol, 20 g of pure water, 14 g of the siloxane compound binder ("MKC (registered trademark) SILICATE MS51" manufactured by Mitsubishi Chemical Corporation), and 2.88 g of the dispersant ("DISPERBYK (registered trademark)-180" manufactured by BYK-Chemie GmbH), and the antibacterial microparticles were changed to 2.4 g of antibacterial microparticles (silver-supporting glass, manufactured by Fuji Chemical Co., Ltd., ethanol dilution; solid content concentration: 30% by mass) having the average particle size controlled to be 0.7 μm.

Furthermore, Antibacterial Liquid A-9 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-9 was obtained.

Example 10

While 560 g of ethanol was stirred in a vessel, 10 g of pure water, 50 g of a siloxane compound as a binder ("MKC (registered trademark) SILICATE MS51" manufactured by Mitsubishi Chemical Corporation), 15 g of ALUMINUM CHELATE D (aluminum bis(ethyl acetoacetate) mono (acetylacetonate), ethanol dilution; solid content concentration: 1% by mass), 30 g of a nonionic surfactant ("EMALEX 715" manufactured by Nihon Emulsion Co., Ltd., pure water dilution; solid content concentration: 0.5% by mass), 10 g of an anionic surfactant (sodium di(2-ethylhexyl)sulfosuccinate, pure water dilution; solid content concentration: 0.2% by mass), 40 g of silica particles ("SNOWTEX O-33" manufactured by Nissan Chemical Industries, Ltd., pure water dilution; solid content concentration: 33% by mass), and 3.6 g of a dispersant ("DISPERBYK (registered trademark)-180" manufactured by BYK-Chemie GmbH) were sequentially added to the vessel. Subsequently, 1.2 g of antibacterial microparticles (silver-supporting glass, manufactured by Fuji Chemical Industries Co., Ltd., ethanol dilution; solid content concentration: 40% by mass) having the average particle size controlled to be 0.5 μm were added to the vessel, and the mixture was stirred for 20 minutes. Thus, Antibacterial Liquid A-10 was obtained.

Furthermore, Antibacterial Liquid A-10 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-10 was obtained.

Example 11

The composition of the Antibacterial Liquid A-10 was changed. Specifically, Antibacterial Liquid A-11 was obtained in the same manner as in Example 10, except that the amounts of incorporation were changed to 640 g of ethanol, 15 g of pure water, 6 g of the siloxane compound binder ("MKC (registered trademark) SILICATE MS51" manufactured by Mitsubishi Chemical Corporation), 16 g of ALUMINUM CHELATE D (aluminum bis(ethyl acetoacetate) mono(acetylacetonate), ethanol dilution; solid content concentration: 1% by mass), 40 g of the nonionic surfactant ("EMALEX 715" manufactured by Nihon Emulsion Co., Ltd., pure water dilution; solid content concentration: 0.5% by mass), 29 g of the silica particles ("SNOWTEX O-33" manufactured by Nissan Chemical Industries, Ltd., pure water dilution; solid content concentration: 33% by mass), 2.88 g of the dispersant ("DISPERBYK (registered trademark)-180" manufactured by BYK-Chemie GmbH), and 0.8 g of the antibacterial microparticles (silver-supporting glass, manufactured by Fuji Chemical Co., Ltd., ethanol dilution; solid content concentration: 60% by mass) having the average particle size controlled to be 0.5 μm.

Furthermore, Antibacterial Liquid A-11 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-11 was obtained.

In regard to Examples 10 and 11, antibacterial films could also be formed similarly, by adding an appropriate amount of the antibacterial liquid dropwise on a PET base material using a dropper, and then wiping the antibacterial liquid to spread over the base material with a nonwoven fabric ("WYPALL" manufactured by Nippon Paper Crecia Co., Ltd.). Also, the antibacterial liquid could be similarly applied on a PET base material, by impregnating a nonwoven fabric ("WYPALL" manufactured by Nippon Paper Crecia Co., Ltd.) with the antibacterial liquid to obtain a wet wipe.

Example 12

While 350 g of ethanol was stirred in a vessel, 135 g of pure water, 4.9 g of a siloxane compound as a binder ("MKC (registered trademark) SILICATE MS51" manufactured by Mitsubishi Chemical Corporation), 16 g of ALUMINUM CHELATE D (aluminum bis(ethyl acetoacetate) mono (acetylacetonate), ethanol dilution; solid content concentration: 1% by mass), and 60 g of a nonionic surfactant ("EMALEX 715" manufactured by Nihon Emulsion Co., Ltd., pure water dilution; solid content concentration: 0.5% by mass) were sequentially added to the vessel. Subsequently, 6 g of antibacterial microparticles (silver-supporting apatite, manufactured by Fuji Chemical Industries Co., Ltd., ethanol dilution; solid content concentration: 20% by mass) having the average particle size controlled to be 1.0 μm were added to the vessel, and the mixture was stirred for 20 minutes. Thus, Antibacterial Liquid A-12 was obtained.

Furthermore, Antibacterial Liquid A-12 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-12 was obtained.

Example 13

The composition of the Antibacterial Liquid A-1 was changed. Specifically, Antibacterial Liquid A-13 was obtained in the same manner as in Example 1, except that the amounts of incorporation were changed to 40 g of ethanol, 430 g of pure water, 5 g of the siloxane compound binder ("MKC (registered trademark) SILICATE MS51" manufactured by Mitsubishi Chemical Corporation), and 2.4 g of the antibacterial microparticles (silver-supporting glass, manufactured by Fuji Chemical Co., Ltd., ethanol dilution; solid content concentration: 50% by mass) having the average particle size controlled to be 1.0 μm.

Furthermore, Antibacterial Film B-13 was obtained in the same manner as in Example 1, using Antibacterial Liquid A-13.

Example 14

While 400 g of ethanol was stirred in a vessel, 30 g of pure water, 9.5 g of a siloxane compound as a binder ("MKC (registered trademark) SILICATE MS51" manufactured by Mitsubishi Chemical Corporation), 15 g of ALUMINUM CHELATE D (aluminum bis(ethyl acetoacetate) mono (acetylacetonate), ethanol dilution; solid content concentration: 1% by mass), 40 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 2.16 g of a dispersant ("DISPERBYK (registered trademark)-180" manufactured by BYK-Chemie GmbH), and 2.4 g of antibacterial microparticles (silver-supporting glass, manufactured by Fuji Chemical Industries Co., Ltd., ethanol dilution; solid content concentration: 30% by mass) having the average particle size controlled to be 0.7 μm were added to the vessel, and the mixture was stirred for 20 minutes. Thus, Antibacterial Liquid A-14 was obtained.

Furthermore, Antibacterial Liquid A-14 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-14 was obtained.

Example 15

The composition of the Antibacterial Liquid A-14 was changed. Specifically, Antibacterial Liquid A-15 was obtained in the same manner as in Example 14, except that the amount of incorporation was changed to 2.88 g of the dispersant ("DISPERBYK (registered trademark)-180" manufactured by BYK-Chemie GmbH), and the antibacterial microparticles were changed to 2.4 g of antibacterial microparticles (silver-supporting glass, manufactured by Fuji Chemical Co., Ltd., ethanol dilution; solid content concentration: 60% by mass) having the average particle size controlled to be 0.5 μm.

Furthermore, Antibacterial Liquid A-15 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-15 was obtained.

Example 16

While 360 g of ethanol was stirred in a vessel, 60 g of pure water, 14 g of a siloxane compound as a binder ("MKC (registered trademark) SILICATE MS51" manufactured by Mitsubishi Chemical Corporation), 15 g of ALUMINUM CHELATE D (aluminum bis(ethyl acetoacetate) mono (acetylacetonate), ethanol dilution; solid content concentration: 1% by mass), 60 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 18 g of isopropanol, 3.6 g of a dispersant ("DISPERBYK (registered trademark)-180" manufactured by BYK-Chemie GmbH), and 2.4 g of antibacterial microparticles (silver-supporting glass, manufactured by Fuji Chemical Industries Co., Ltd., ethanol dilution; solid content concentration: 60% by mass) having the average particle size controlled to be 0.5 µm were added to the vessel, and the mixture was stirred for 20 minutes. Thus, Antibacterial Liquid A-16 was obtained.

Furthermore, Antibacterial Liquid A-16 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-16 was obtained.

In regard to Examples 15 and 16, antibacterial films could also be formed similarly, by adding an appropriate amount of the antibacterial liquid dropwise on a PET base material using a dropper, and then wiping the antibacterial liquid to spread over the base material with a nonwoven fabric ("BEMCOT" manufactured by Asahi Kasei Corporation). Also, the antibacterial liquid could be similarly applied on a PET base material, by impregnating a nonwoven fabric ("BEMCOT" manufactured by Asahi Kasei Corporation) with the antibacterial liquid to obtain a wet wipe.

Example 17

The composition of the Antibacterial Liquid A-16 was changed. Specifically, Antibacterial Liquid A-17 was obtained in the same manner as in Example 16, except that isopropanol was changed to methanol.

Furthermore, Antibacterial Liquid A-17 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-17 was obtained.

Example 18

The composition of the Antibacterial Liquid A-4 was changed. Specifically, Antibacterial Liquid A-18 was obtained in the same manner as in Example 4, except that 29 g of a siloxane compound as a binder ("MKC (registered trademark) SILICATE MS51" manufactured by Mitsubishi Chemical Corporation), and 14 g of antibacterial microparticles (silver-supporting glass, manufactured by Fuji Chemical Co., Ltd., ethanol dilution; solid content concentration: 50% by mass) having the average particle size controlled to be 1.0 µm were added to the mixture.

Furthermore, Antibacterial Liquid A-18 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-18 was obtained.

Example 19

The composition of the Antibacterial Liquid A-4 was changed. Specifically, Antibacterial Liquid A-19 was obtained in the same manner as in Example 4, except that 350 g of ethanol, 250 g of pure water, 25 g of a siloxane compound as a binder ("MKC (registered trademark) SILICATE MS51" manufactured by Mitsubishi Chemical Corporation), and 14 g of antibacterial microparticles (silver-supporting glass, manufactured by Fuji Chemical Co., Ltd., ethanol dilution; solid content concentration: 50% by mass) having the average particle size controlled to be 1.0 µm were added to the mixture.

Furthermore, Antibacterial Liquid A-19 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-19 was obtained.

Example 20

The composition of the Antibacterial Liquid A-12 was changed. Specifically, Antibacterial Liquid A-20 was obtained in the same manner as in Example 12, except that the antibacterial microparticles (silver-supporting apatite) were changed to 2 g of antibacterial microparticles (silver-supporting glass, manufactured by Fuji Chemical Co., Ltd., ethanol dilution; solid content concentration: 50% by mass) having the average particle size controlled to be 1.0 µm.

Furthermore, Antibacterial Liquid A-20 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-20 was obtained.

Example 21

While 600 g of ethanol was stirred in a vessel, 8 g of pure water, 5 g of a siloxane compound as a binder ("MKC (registered trademark) SILICATE MS51" manufactured by Mitsubishi Chemical Corporation), 16 g of ALUMINUM CHELATE D (aluminum bis(ethyl acetoacetate) mono (acetylacetonate), ethanol dilution; solid content concentration: 1% by mass), 40 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 30 g of isopropanol, 0.6 g of a dispersant ("DISPERBYK (registered trademark)-180" manufactured by BYK-Chemie GmbH), and 0.8 g of antibacterial microparticles (silver-supporting glass, manufactured by Fuji Chemical Industries Co., Ltd., ethanol dilution; solid content concentration: 25% by mass) having the average particle size controlled to be 0.5 µm were added to the vessel, and the mixture was stirred for 20 minutes. Thus, Antibacterial Liquid A-21 was obtained.

Furthermore, Antibacterial Liquid A-21 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-21 was obtained.

Example 22

The composition of the Antibacterial Liquid A-21 was changed. Specifically, Antibacterial Liquid A-22 was obtained in the same manner as in Example 21, except that 3.5 g of citric acid was further incorporated into the mixture, and the mixture was stirred.

Furthermore, Antibacterial Liquid A-22 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-22 was obtained.

Example 23

The composition of the Antibacterial Liquid A-21 was changed. Specifically, Antibacterial Liquid A-23 was obtained in the same manner as in Example 21, except that 3.5 g of malic acid was further incorporated into the mixture, and the mixture was stirred.

Furthermore, Antibacterial Liquid A-23 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-23 was obtained.

Example 24

While 830 g of ethanol was stirred in a vessel, 66 g of pure water, 0.8 g of a siloxane compound as a binder ("MKC (registered trademark) SILICATE MS51" manufactured by Mitsubishi Chemical Corporation), 2.3 g of ALUMINUM CHELATE D (aluminum bis(ethyl acetoacetate) mono (acetylacetonate), ethanol dilution; solid content concentration: 1% by mass), 6 g of a nonionic surfactant ("EMALEX 715" manufactured by Nihon Emulsion Co., Ltd., pure water dilution; solid content concentration: 0.5% by mass), and 1.5 g of an anionic surfactant (sodium di(2-ethylhexyl)sulfosuccinate, pure water dilution; solid content concentration: 0.2% by mass) were sequentially added to the vessel. Subsequently, 4.5 g of isopropanol, 0.08 g of a dispersant ("DISPERBYK (registered trademark)-180" manufactured by BYK-Chemie GmbH), and 0.105 g of antibacterial microparticles (silver-supporting glass, manufactured by Fuji Chemical Industries Co., Ltd., ethanol dilution; solid content concentration: 25.4% by mass) having the average particle size controlled to be 0.5 μm were added to the vessel, and the mixture was stirred for 20 minutes. Thus, Antibacterial Liquid A-24 was obtained.

Furthermore, Antibacterial Liquid A-24 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film B-24 was obtained.

Comparative Example 1

While 470 g of pure water was stirred in a vessel, 60 g of ALUMINUM CHELATE D (aluminum bis(ethyl acetoacetate) mono(acetylacetonate), pure water dilution; solid content concentration: 1% by mass), 60 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 2.5 g of antibacterial microparticles (silver-supporting glass, manufactured by Fuji Chemical Industries Co., Ltd., pure water dilution; solid content concentration: 50% by mass) having the average particle size controlled to be 3.0 μm were added to the vessel, and the mixture was stirred for 20 minutes. Thus, Antibacterial Liquid C-1 was obtained.

Furthermore, Antibacterial Liquid C-1 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film D-1 was obtained.

Comparative Example 2

While 33 g of ethanol was stirred in a vessel, 460 g of pure water, 9 g of a siloxane compound as a binder ("MKC (registered trademark) SILICATE MS51" manufactured by Mitsubishi Chemical Corporation), 15 g of ALUMINUM CHELATE D (aluminum bis(ethyl acetoacetate) mono (acetylacetonate), ethanol dilution; solid content concentration: 1% by mass), 60 g of a nonionic surfactant ("EMALEX 715" manufactured by Nihon Emulsion Co., Ltd., pure water dilution; solid content concentration: 0.5% by mass), and 10 g of an anionic surfactant (sodium di(2-ethylhexyl)sulfosuccinate, pure water dilution; solid content concentration: 0.2% by mass) were sequentially added to the vessel. Subsequently, 9 g of antibacterial microparticles (silver-supporting glass, manufactured by Fuji Chemical Industries Co., Ltd., pure water dilution; solid content concentration: 80% by mass) having the average particle size controlled to be 2.0 μm were added to the vessel, and the mixture was stirred for 20 minutes. Thus, Antibacterial Liquid C-2 was obtained.

Furthermore, Antibacterial Liquid C-2 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film D-2 was obtained.

Comparative Example 3

While 470 g of pure water was stirred in a vessel, 60 g of a nonionic surfactant ("EMALEX 715" manufactured by Nihon Emulsion Co., Ltd., pure water dilution; solid content concentration: 0.5% by mass) and 10 g of an anionic surfactant (sodium di(2-ethylhexyl)sulfosuccinate, pure water dilution; solid content concentration: 0.2% by mass) were sequentially added to the vessel. Subsequently, 10 g of malic acid and 2.5 g of antibacterial microparticles (silver-supporting glass, manufactured by Fuji Chemical Industries Co., Ltd., pure water dilution; solid content concentration: 50% by mass) having the average particle size controlled to be 3.0 μm were added to the vessel, and the mixture was stirred for 20 minutes. Thus, Antibacterial Liquid C-3 was obtained.

Furthermore, Antibacterial Liquid C-3 was applied, using a bar coater, on a PET base material that had been subjected to an easy adhesion treatment on one surface, the antibacterial liquid being applied on the easy adhesion-treated surface, and the antibacterial liquid was dried at room temperature for 20 minutes. Thus, Antibacterial Film D-3 was obtained.

<Physical Properties of Antibacterial Liquid and Antibacterial Film>

For the various antibacterial liquids, viscosity (unit: cP) at 25° C., turbidity (unit: ppm), pH, and surface tension (unit: mN/m) were determined by the measurement methods described above.

In regard to viscosity and turbidity, an antibacterial liquid was introduced into a glass bottle with a cap, and the amount of change in the case of storing the antibacterial liquid for 500 hours in a low-temperature environment at a temperature of 5° C. and the amount of change in the case of storing the antibacterial liquid for 500 hours in a high-temperature environment at a temperature of 40° C. and a relative humidity of 80% were also determined.

Furthermore, for the various antibacterial films, the film thickness (average film thickness, unit: μm) and the water contact angle (unit: °) were determined by the measurement methods described above. Furthermore, double coating was performed, and the absolute value of the difference in the water contact angle (|X−Y|) was also determined. The results are all presented in the following Table 1 and Table 2.

<Evaluation>

For the various antibacterial liquids and various antibacterial films, the following evaluations were performed. The results are presented in the following Table 1 and Table 2. In a case in which an evaluation was not performed, the symbol "-" is described in the tables.

(Sedimentation Resistance)

Various antibacterial liquids were stored by leaving the liquids to stand at room temperature, and the presence or absence of sedimentation was checked by visual inspection. Sedimentation resistance was evaluated according to the following criteria, based on the time in which sedimentation could be suppressed. For practical use, grade "S", "A", "B", "B−", or "C" is preferable.

"S": 300 hours or longer
"A": 100 hours or longer and shorter than 300 hours
"B": 72 hours or longer and shorter than 100 hours
"B−": 48 hours or longer and shorter than 72 hours
"C": 24 hours or longer and shorter than 48 hours
"D": Shorter than 24 hours (sedimentation was saturated at the time point at which 24 hours had lapsed)

(Antibacterial Properties)

In regard to the evaluation of antibacterial properties of antibacterial films, the test was performed according to the evaluation method described in JIS Z 2801, by changing the contact time with a bacterial solution to 3 hours. The antibacterial activity value after the test was measured, and the evaluation was performed according to the following criteria. For practical use, grade "A", "B", or "C" is preferable.

"A": The antibacterial activity value is 3.5 or higher.
"B": The antibacterial activity value is 2.0 or higher and lower than 3.5.
"C": The antibacterial activity value is 1.0 or higher and lower than 2.0.
"D": The antibacterial activity value is lower than 1.0.

(Antifouling Properties)

Antifouling properties were evaluated based on the water contact angles of antibacterial films. In a case in which the water contact angle was smaller than 20°, the sample was rated as "A"; in a case in which the water contact angle was 200 or larger and smaller than 40°, the sample was rated as "B"; in a case in which the water contact angle was from 40° to 60°, the sample was rated as "C"; and in a case in which the water contact angle was larger than 60°, the sample was rated as "D".

(Overcoating Properties)

A nonwoven fabric ("WYPALL" manufactured by Nippon Paper Crecia Co., Ltd.) was impregnated with an antibacterial liquid in a mass amount equivalent to four times the mass of the nonwoven fabric, and this was used as a wet wipe.

The antibacterial liquid was applied on the surface of a transparent PET base material using this wet wipe, and the antibacterial liquid was dried at room temperature for 20 minutes. Thus, an antibacterial film was formed. Subsequently, the antibacterial liquid was applied similarly on the antibacterial film that had been already formed, using a fresh wet wipe, and thus an antibacterial film was formed. Such application of the antibacterial liquid and formation of the antibacterial films were repeated 50 times.

For the antibacterial film after the first application and the antibacterial film after the $50^{th}$ application, the respective haze values were measured. The difference between the haze values thus measured was determined as the amount of change in the haze value (unit: %), and an evaluation was performed according to the following criteria. For the measurement of the haze values, a haze meter, NDH5000, manufactured by Nippon Denshoku Industries Co., Ltd. was used.

It can be evaluated such that as the amount of change in the haze value is smaller, the effect of suppressing whitening of the antibacterial film obtainable by overcoating is excellent. For practical use, grade "A", "B", or "C" is preferable, and grade "A" or "B" is more preferable.

"A": The amount of change in the haze value is less than 3.
"B": The amount of change in the haze value is 3 or greater and less than 10.
"C": The amount of change in the haze value is 10 or greater.
"D": The amount of change in the haze value is 15 or greater.

(Antiviral Properties)

The antiviral properties of antibacterial liquids were evaluated as follows.

First, a viral solution of feline calicivirus (alternative of norovirus) that had been adjusted to $5 \times 10^6$ PFU/mL was added dropwise to an antibacterial liquid in an equal amount. The mixture was stirred for 10 seconds and then was left to stand for one minute at 25° C. Subsequently, the liquid was collected and thoroughly mixed with SCDLP medium. The mixture thus obtained was inoculated in an amount of 0.1 mL each to CRFK cells that had been cultured on a six-well plate, and the mixture was adsorbed thereto for one hour at 37° C. Subsequently, the inoculation liquid was washed away, an agar medium was overlaid, and the cells were cultured for two days. The number of plaques after culturing was counted, and the antiviral activity value was calculated using the following formula.

$$Mv = lg(Va) - lg(Vb)$$

Here, Mv: antiviral activity value, lg(Va): common logarithm of the viral infectivity titer of the liquid as an object of comparison, lg(Vb): common logarithm of the viral infectivity titer of the antibacterial liquid of an Example or a Comparative Example. Sterilized distilled water was used as the liquid as an object of comparison, and the same test as the above-described test was performed. An evaluation was performed according to the following criteria. For practical use, grade "A", "B", "C", or "D" is preferable, and grade "A" or "B" is more preferable.

PFU is an abbreviation for "Plaque Forming Unit", SCDLP is an abbreviation for "Soybean-Casein Digest Agar with Lecithin & Polysorbate 80", and CRFK is an abbreviation for "Crandell Rees Feline Kidney".

"A": The antiviral activity value is 3.0 or higher.
"B": The antiviral activity value is 2.0 or higher and lower than 3.0.
"C": The antiviral activity value is 1.0 or higher and lower than 2.0.
"D": The antiviral activity value is 0.2 or higher and lower than 1.0.
"E": The antiviral activity value is lower than 0.2.

TABLE 1

| | Antibacterial microparticles | | | | | Dispersant | | | | | |
|---|---|---|---|---|---|---|---|---|---|---|---|
| | Silver-supporting inorganic oxide | Average particle size [μm] | Solid content (with respect to total mass) [% by mass] | Solid content (with respect to total solid content mass) [% by mass] | Binder Type | Solvent Alcohol content (with respect to total mass) [% by mass] | Silica particles | Dispersant | content (with respect to antibacterial microparticles) [% by mass] | Viscosity at 25° C. [cP] | Turbidity [ppm] |
| Example 1 | Silver-supporting glass | 1.0 | 0.2 | 17.5 | Siloxane compound | 50 | Absent | Absent | — | 3.5 | 80 |
| Example 2 | Silver-supporting glass | 1.0 | 0.2 | 17.5 | Siloxane compound | 65 | Absent | Absent | — | 3.0 | 65 |
| Example 3 | Silver-supporting glass | 1.0 | 0.2 | 17.5 | Siloxane compound | 80 | Absent | Absent | — | 2.8 | 50 |
| Example 4 | Silver-supporting glass | 1.0 | 1.0 | 19 | Siloxane compound | 50 | Absent | Absent | — | 3.8 | 85 |
| Example 5 | Silver-supporting glass | 1.0 | 0.2 | 5 | Siloxane compound | 65 | Present | Absent | — | 3.8 | 66 |
| Example 6 | Silver-supporting glass | 1.0 | 0.2 | 5 | Siloxane compound | 65 | Present | Absent | — | 3.8 | 66 |
| Example 7 | Silver-supporting glass | 1.0 | 0.2 | 4 | Siloxane compound | 65 | Present | Present | 50 | 3.8 | 66 |
| Example 8 | Silver-supporting glass | 1.0 | 0.2 | 4 | Siloxane compound | 65 | Present | Present | 300 | 3.8 | 66 |
| Example 9 | Silver-supporting glass | 0.7 | 0.1 | 2.5 | Siloxane compound | 80 | Present | Present | 400 | 2.8 | 30 |
| Example 10 | Silver-supporting glass | 0.5 | 0.1 | 1 | Siloxane compound | 80 | Present | Present | 500 | 2.8 | 25 |
| Example 11 | Silver-supporting glass | 0.5 | 0.06 | 2.5 | Siloxane compound | 86 | Present | Present | 600 | 2.0 | 18 |
| Example 12 | Silver-supporting glass | 1.0 | 0.2 | 18.3 | Siloxane compound | 65 | Absent | Absent | — | 3.0 | 95 |
| Example 13 | Silver-supporting glass | 1.0 | 0.2 | 18 | Siloxane compound | 10 | Absent | Absent | — | 4.0 | 90 |

| | | | Amount of change (viscosity/turbidity) | | | Average particle size/film thickness (B/A) | Water contact angle [°] | Difference of water contact angle ($|X - Y|$) [°] | Evaluation | | | | |
|---|---|---|---|---|---|---|---|---|---|---|---|---|---|
| | pH | Surface tension [mN/m] | 5° C. 500 h | 40° C. RH80% 500 h | Film thickness [μm] | | | | Sedimentation resistance | Antibacterial properties | Antifouling properties | Overcoating properties | Antiviral properties |
| Example 1 | 5.6 | 33 | 1/7 | 0.8/20 | 1.0 | 1 | 40 | 8 | B | B | C | B | B |
| Example 2 | 5.8 | 28 | 0.5/7 | 0.8/20 | 1.0 | 1 | 35 | 7 | B | B | B | B | B |
| Example 3 | 6.2 | 25 | 0.5/5 | 0.8/10 | 1.0 | 1 | 30 | 8 | B | B | B | B | C |
| Example 4 | 4.4 | 30 | 0.7/9 | 1/20 | 1.0 | 1 | 33 | 9 | B | A | B | C | A |
| Example 5 | 5.8 | 27 | 0.5/6 | 0.4/10 | 1.0 | 1 | 19 | 9 | B | B | A | B | B |
| Example 6 | 5.8 | 27 | 0.5/6 | 0.4/10 | 0.5 | 2 | 18 | 6 | B | B | A | B | B |
| Example 7 | 7.1 | 25 | 0.5/6 | 0.4/10 | 0.5 | 2 | 18 | 6 | A | A | A | B | C |
| Example 8 | 8.5 | 26 | 0.5/3 | 0.4/6 | 1.0 | 1 | 19 | 7 | A | A | A | B | D |
| Example 9 | 6.9 | 25 | 0.3/3 | 0.5/8 | 0.5 | 1.4 | 17 | 4 | S | A | A | B | C |
| Example 10 | 7.2 | 25 | 0.3/2 | 0.5/6 | 0.3 | 1.66 | 18 | 3 | S | A | A | B | C |
| Example 11 | 6.8 | 23 | 0.3/2 | 0.5/4 | 0.3 | 1.66 | 18 | 3 | S | A | A | B | C |

TABLE 1-continued

| | | | | | | | | | | | | | |
|---|---|---|---|---|---|---|---|---|---|---|---|---|---|
| Example 12 | 5.5 | 33 | 0.8/8 | 2/20 | 1.0 | 1 | 37 | 8 | B | C | B | B | B |
| Example 13 | 8.5 | 40 | 0.8/8 | 0.8/20 | 1.0 | 1 | 54 | 10 | C | C | C | B | D |

TABLE 2

| | Antibacterial microparticles | | | | | | | | Dispersant | | |
|---|---|---|---|---|---|---|---|---|---|---|---|
| | Silver-supporting inorganic oxide | Average particle size [μm] | Solid content (with respect to total mass) [% by mass] | Solid content (with respect to total solid content mass) [% by mass] | Binder Type | Solvent Alcohol content (with respect to total mass) [% by mass] | Silica particles | Dispersant | content (with respect to antibacterial microparticles) [% by mass] | Viscosity at 25° C. [cP] | Turbidity [ppm] |
| Example 14 | Silver-supporting glass | 0.7 | 0.14 | 5.6 | Siloxane compound | 82 | Absent | Present | 300 | 2.9 | 35 |
| Example 15 | Silver-supporting glass | 0.5 | 0.28 | 10 | Siloxane compound | 82 | Absent | Present | 200 | 2.8 | 33 |
| Example 16 | Silver-supporting glass | 0.5 | 0.27 | 7.4 | Siloxane compound | 73 | Absent | Present | 250 | 2.8 | 32 |
| Example 17 | Silver-supporting glass | 0.5 | 0.27 | 7.4 | Siloxane compound | 73 | Absent | Present | 250 | 2.6 | 32 |
| Example 18 | Silver-supporting glass | 1.0 | 1.2 | 19 | Siloxane compound | 50 | Absent | Absent | — | 3.7 | 85 |
| Example 19 | Silver-supporting glass | 1.0 | 1.0 | 22 | Siloxane compound | 50 | Absent | Absent | — | 3.2 | 70 |
| Example 20 | Silver-supporting glass | 1.0 | 0.18 | 15.7 | Siloxane compound | 65 | Absent | Absent | — | 3.0 | 86 |
| Example 21 | Silver-supporting glass | 0.5 | 0.03 | 3.2 | Siloxane compound | 91 | Absent | Present | 300 | 2.1 | 18 |
| Example 22 | Silver-supporting glass | 0.5 | 0.03 | 2.1 | Siloxane compound | 91 | Absent | Present | 300 | 2.8 | 25 |
| Example 23 | Silver-supporting glass | 0.5 | 0.03 | 2.1 | Siloxane compound | 91 | Absent | Present | 300 | 3.0 | 23 |
| Example 24 | Silver-supporting glass | 0.5 | 0.003 | 2.8 | Siloxane compound | 92 | Absent | Present | 300 | 2.0 | 9 |
| Comparative Example 1 | Silver-supporting glass | 3.0 | 0.2 | 58 | — | — | Absent | Absent | — | 2.2 | 110 |
| Comparative Example 2 | Silver-supporting glass | 2.0 | 1.2 | 43 | Siloxane compound | 8 | Absent | Absent | — | 5.2 | 120 |
| Comparative Example 3 | Silver-supporting glass | 3.0 | 0.23 | 10.8 | — | — | Absent | Absent | — | 2.2 | 110 |

| | | | Amount of change (viscosity/turbidity) | | | Average | Water | Difference of water contact | Evaluation | | | | |
|---|---|---|---|---|---|---|---|---|---|---|---|---|---|
| | pH | Surface tension [mN/m] | 5° C. 500 h | 40° C. RH80% 500 h | Film thickness [μm] | particle size/film thickness (B/A) | contact angle [°] | angle (\|X − Y\|) [°] | Sedimentation resistance | Antibacterial properties | Antifouling properties | Overcoating properties | Antiviral properties |
| Example 14 | 7.0 | 25 | 0.5/3 | 0.4/7 | 1.0 | 0.7 | 37 | 8 | S | A | B | B | C |
| Example 15 | 6.8 | 29 | 0.3/2 | 0.4/5 | 0.5 | 1 | 36 | 7 | S | A | B | C | C |
| Example 16 | 6.9 | 25 | 0.3/2 | 0.5/5 | 0.5 | 1 | 36 | 8 | S | A | B | C | C |
| Example 17 | 7.0 | 25 | 0.3/3 | 0.5/4 | 0.5 | 1 | 37 | 7 | S | A | B | C | C |
| Example 18 | 4.4 | 32 | 0.8/9 | 1/18 | 1.0 | 1 | 33 | 10 | B− | A | B | C | A |
| Example 19 | 4.8 | 30 | 1/9 | 1.3/20 | 1.0 | 1 | 33 | 10 | B− | B | B | C | A |
| Example 20 | 5.8 | 35 | 0.5/6 | 1/15 | 1.0 | 1 | 28 | 7 | B | B | B | B | B |
| Example 21 | 6.8 | 25 | 0.5/2 | 0.4/5 | 0.3 | 1.66 | 38 | 8 | S | A | B | B | C |
| Example 22 | 4.8 | 24 | 0.5/7 | 0.8/10 | 0.3 | 1.66 | 40 | 9 | S | A | B | B | A |
| Example 23 | 4.6 | 24 | 0.5/5 | 0.8/11 | 0.3 | 1.66 | 40 | 8 | S | A | B | B | A |
| Example 24 | 6.8 | 25 | 0.5/2 | 0.4/5 | 0.3 | 1.66 | 38 | 8 | S | A | B | A | C |

TABLE 2-continued

| | | | | | | | | | | | | | |
|---|---|---|---|---|---|---|---|---|---|---|---|---|---|
| Comparative Example 1 | 8.8 | 68 | 2.2/15 | 2.2/36 | 0.2 | 15 | 80 | 11 | D | D | D | — | E |
| Comparative Example 2 | 4.9 | 42 | 1.2/15 | 1.2/46 | 1.5 | 1.33 | 58 | 13 | D | C | C | D | D |
| Comparative Example 3 | 4.5 | 68 | 2.2/10 | 2.2/36 | 0.2 | 15 | 80 | 11 | D | D | D | — | D |

As is obvious from Table 1 and Table 2 described above, Comparative Examples 1 to 3, in which the average particle size of the antibacterial microparticles was greater than 1.0 µm and the content of the alcohol was less than 10% by mass, exhibited insufficient sedimentation resistance. Furthermore, Comparative Examples 1 and 3 that did not include any siloxane compound and had a water contact angle of 80°, also exhibited insufficient antibacterial properties.

In contrast, Examples 1 to 24 all exhibited satisfactory sedimentation resistance and antibacterial properties.

Examples 9 to 11 and 14 to 17, in which the average particle size of the antibacterial microparticles was 0.7 µm or less, exhibited more satisfactory sedimentation resistance.

As a comparison was made between Example 4 and Example 18, Example 4 in which the content of the antibacterial microparticles with respect to the total mass of the antibacterial liquid was 1.0% by mass or less as solid content, exhibited more satisfactory sedimentation resistance than Example 18.

Furthermore, as a comparison was made between Example 4 and Example 19, Example 4 in which the content of the antibacterial microparticles with respect to the total solid content mass of the antibacterial liquid was 20% by mass or less as solid content, exhibited more satisfactory sedimentation resistance than Example 19.

As a comparison was made between Example 12 and Example 20, Example 20 that used silver-supporting glass as the antibacterial microparticles (silver-supporting inorganic oxide) exhibited more satisfactory antibacterial properties than Example 12.

As a comparison was made among Examples 1 to 24, it was found that a case in which the content of the antibacterial microparticles with respect to the total mass of the antibacterial liquid was 0.2% by mass or less as solid content, more satisfactory overcoating was achieved than the case in which the content of the antibacterial microparticles was more than 0.2% by mass.

Furthermore, as a comparison was made among Examples 1 to 24 in which the alcohol content (with respect to the total mass) in the antibacterial liquid was 10% by mass or more, in a case in which the pH of the antibacterial liquid was 6 or lower, more satisfactory antiviral properties was achieved than the case in which the pH of the antibacterial liquid was higher than 6.

From the results of Comparative Example 3, it was found that even in a case in which the pH of the antibacterial liquid was lowered by incorporating an acidic material, the Example did not show sufficient antiviral properties in a case in which the antibacterial liquid did not contain an alcohol.

FIG. 1 is an electron micrograph of the surface of Antibacterial Film B-8 of Example 8 captured (magnification ratio: 5,000 times) by a scanning electron microscope. Image capturing was carried out after a metal deposit film (metal kind: platinum and palladium) was formed on the surface of the antibacterial film. From the electron micrograph shown in FIG. 1, it was found that antibacterial microparticles are disposed in a convex shape to the antibacterial film. In FIG. 1, a white portion is a convex shaped portion.

What is claimed is:

1. An antibacterial liquid comprising: an antibacterial microparticle; a binder; and a solvent,
    wherein the antibacterial microparticle contains a silver-supporting inorganic oxide,
    the average particle size of the antibacterial microparticles is 0.5 µm to 1.0 µm,
    the binder includes at least one silane compound,
    the solvent includes an alcohol and water,
    the content of the alcohol is 10% by mass or more with respect to the total mass of the antibacterial liquid,
    the alcohol is selected from the group consisting of methanol, ethanol, n-propanol, isopropanol, n-butanol, 2-butanol, i-butanol, t-butanol, n-pentanol, t-amyl alcohol, and n-hexanol, and
    the silane compound is a siloxane compound represented by General Formula (1'):

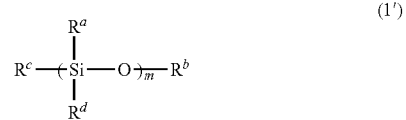

(1')

in General Formula (1'), $R^a$, $R^b$, $R^c$, and $R^d$ each independently represent a hydrogen atom or an organic group, $R^a$ to $R^d$ may be respectively identical with or different from each other, and $R^a$ to $R^d$ may be bonded to each other and form a ring, and
    m represents an integer from 1 to 100.

2. The antibacterial liquid according to claim 1, wherein the average particle size of the antibacterial microparticles is 0.5 µm to 0.7 µm.

3. The antibacterial liquid according to claim 1, wherein the silver-supporting inorganic oxide is silver-supporting glass.

4. The antibacterial liquid according to claim 1, wherein the content of the alcohol is 50% by mass or more with respect to the total mass of the antibacterial liquid.

5. The antibacterial liquid according to claim 1, wherein the content of the antibacterial microparticles is, as solid content, 1.0% by mass or less with respect to the total mass of the antibacterial liquid.

6. The antibacterial liquid according to claim 1, wherein the content of the antibacterial microparticles is, as solid content, 0.2% by mass or less with respect to the total mass of the antibacterial liquid.

7. The antibacterial liquid according to claim 1, wherein the content of the antibacterial microparticles is, as solid content, 20% by mass or less with respect to the total solid content mass of the antibacterial liquid.

8. The antibacterial liquid according to claim 1, wherein the viscosity at 25° C. is 0.5 to 5 cP.

9. The antibacterial liquid according to claim 1, wherein the turbidity is 100 ppm or less.

10. The antibacterial liquid according to claim 1, further comprising an anionic dispersant.

11. The antibacterial liquid according to claim 10, wherein the content of the anionic dispersant is 50% by mass or more with respect to the content of the antibacterial microparticles.

12. The antibacterial liquid according to claim 1, wherein in a case in which the antibacterial liquid is stored for 500 hours in a low-temperature environment at a temperature of 5° C., the amount of change in the viscosity at 25° C. is 2 cP or less, and the amount of change in the turbidity is 10 ppm or less.

13. The antibacterial liquid according to claim 1, wherein in a case in which the antibacterial liquid is stored for 500 hours in a high-temperature environment at a temperature of 40° C. and a relative humidity of 80%, the amount of change in the viscosity at 25° C. is 2 cP or less, and the amount of change in the turbidity is 20 ppm or less.

14. The antibacterial liquid according to claim 1, wherein the antibacterial liquid is configured to be applied to a base material as a first bacterial film, and is configured to be applied to the first bacterial film as a second bacterial film, such that an absolute value of the difference between the water contact angle X of the first antibacterial film and the water contact angle Y of the second antibacterial film, |X−Y|, is 10° or less.

15. The antibacterial liquid according to claim 1, wherein the antibacterial liquid has a pH of 6 or lower.

16. An antibacterial film formed using the antibacterial liquid according to claim 1.

17. The antibacterial film according to claim 16, wherein the antibacterial film has a water contact angle of 60° or less.

18. The antibacterial film according to claim 16, wherein the ratio B/A of the average particle size B of the antibacterial microparticles with respect to the film thickness A is 1 or greater.

19. The antibacterial film according to claim 16, wherein the antibacterial film has a film thickness of 1.0 μm or less.

20. A wet wipe comprising a base fabric impregnated with the antibacterial liquid according to claim 1.

21. The antibacterial liquid according to claim 1, wherein the antibacterial liquid further comprises silica particles.

22. The antibacterial liquid according to claim 1, wherein the content of the binder with respect to the total mass of the antibacterial liquid is 10% by mass or less.

23. The antibacterial liquid according to claim 1, wherein the content of the binder with respect to the total mass of the antibacterial liquid is 3% by mass or less.

* * * * *